United States Patent [19]

Dixon et al.

[11] 4,260,748

[45] Apr. 7, 1981

[54] MORPHOLINE FROM BIS (CYANOMETHYL) ETHER

[75] Inventors: Dale D. Dixon, Kutztown; Randall J. Daughenbaugh, Barto, both of Pa.

[73] Assignee: Air Products and Chemicals, Inc., Allentown, Pa.

[21] Appl. No.: 128,073

[22] Filed: Mar. 7, 1980

[51] Int. Cl.$^3$ .................................... C07D 295/02
[52] U.S. Cl. ................... 544/106; 564/490; 564/508
[58] Field of Search ................................ 544/106

[56] References Cited

U.S. PATENT DOCUMENTS

| | | | |
|---|---|---|---|
| 2,701,263 | 2/1955 | Wielicki et al. | 260/583 K |
| 3,427,322 | 2/1969 | Argabright et al. | 260/340.6 |

*Primary Examiner*—John D. Randolph
*Assistant Examiner*—R. W. Ramsuer
*Attorney, Agent, or Firm*—E. Eugene Innis; Russell L. Brewer

[57] ABSTRACT

Morpholine is produced by the catalytic hydrogenation of bis (cyanomethyl) ether.

4 Claims, No Drawings

MORPHOLINE FROM BIS (CYANOMETHYL) ETHER

DESCRIPTION OF THE PRIOR ART

U.S. Pat. No. 3,427,322 discloses a method for producing bis (cyanomethyl) ether involving the reaction of bis (chloromethyl) ether with sodium cyanide. The reaction is carried out in the presence of dimethylformamide solvent. The compound has alleged utility for preparing the diamine.

U.S. Pat. No. 2,701,263 discloses a process for preparing bis (3-aminopropyl) ether by catalytically hydrogenating bis (2-cyanoethyl) ether.

SUMMARY OF THE INVENTION

This invention relates to a process for producing morpholine by the catalytic hydrogenation of bis (cyanomethyl) ether. During hydrogenation of the bis (cyanomethyl) ether the nitrile group is reduced and cyclization occurs to form the heterocyclic amine.

One of the distinct advantages of this process is that morpholine, which is highly desirable from a commercial point of view, can be prepared from relatively simple feedstocks of formaldehyde and hydrogen cyanide. These components are used to form the bis (cyanomethyl) ether which then can be hydrogenated using a typical hydrogenation technique to form morpholine product.

DESCRIPTION OF THE PREFERRED EMBODIMENTS

Bis (cyanomethyl) ether is a known composition and as mentioned previously a method of manufacture is found in U.S. Pat. No. 3,427,322 and such method is incorporated by reference. Typically the reaction for the preparation of the bis (cyanomethyl) ether is based upon the reaction of sodium cyanide and bis (chloromethyl) ether.

Surprisingly, in contrast to what might be suspected by conventional hydrogenation of bis (cyanomethyl) ether, a heterocyclic amine namely morpholine is produced. It was anticipated that the diamine namely bis (2-aminoethyl) ether would be produced by the reduction.

The process conditions used for the manufacture of morpholine by the hydrogenation of bis (cyanomethyl ether play an important role inthe product produced. Typically, the temperature of hydrogenation is from about 25° to 350° C. and preferably from about 50° to 300° C. Additionally, the pressure of the reaction is maintained at about 0 to 6,000 psig, and preferably 50 to 500 psig. Lower pressures afford slightly lower conversions.

The reduction can be carried out using conventional hydrogenation/dehydrogenation catalysts but typically catalysts which include the metals from the Group 6 and group 8 classes which are used for hydrogenation of nitriles. Generally, the catalysts used are nickel containing catalysts e.g. nickel-chromium, nickel-copper and the like.

The following examples are provided to illustrate preferred embodiments of the invention.

EXAMPLE 1

A 1.5 gram portion of bis (cyanomethyl) ether was dissolved in a 150 ml of diethyl ether and then resulting solution was added to a 300 ml stirred autoclave. The catalyst to be used for the hydrogenation consisted of 4.0 grams of Raney nickel catalyst code number 28 by the W. R. Grace Company. The catalyst was vacuum filtered, washed with methanol and added to the autoclave. The autoclave was sealed, purged twice with nitrogen at 4,000 psig, and then twice with hydrogen. After venting, the reactor was then pressurized to 4,000 psi with hydrogen.

The reaction was carried out by heating the contents to 70° C. and agitating for a period of 4 hours. At the end of 4 hours the reduction was deemed complete and then the reactor was allowed to cool to room temperature. The diethylether solution was removed and decanted from the Raney nickel catalyst. Gas Chromotography was used to analyze the major components of the reactor products. The analyses revealed the product contained 46% morpholine and 19% bis (2-aminoethyl) ether.

What is claimed is:

1. A process for producing morpholine which comprises:
   hydrogenating bis (cyanomethyl) ether in the presence of a hydrogenation catalyst, whereby cyclization of the ether to the heterocyclic amine is achieved.

2. The process of claim 1 wherein the temperature of the hydrogenation is from about 50° to 300° C.

3. The process of claim 2 wherein the pressure carried out during hydrogenation is from about 50 to 500 psig.

4. The process of claim 3 wherein the catalyst used for the hydrogenation is a nickel containing catalyst.

* * * * *